US006642062B2

(12) United States Patent
Kauvar et al.

(10) Patent No.: US 6,642,062 B2
(45) Date of Patent: Nov. 4, 2003

(54) MULTIHUED LABELS

(75) Inventors: Lawrence M. Kauvar, San Francisco, CA (US); John Sedat, San Francisco, CA (US)

(73) Assignee: Trellis Bioinformatics, Inc., San Francisco, CA (US)

(*) Notice: Subject to any disclaimer, the term of this patent is extended or adjusted under 35 U.S.C. 154(b) by 0 days.

(21) Appl. No.: 09/146,984

(22) Filed: Sep. 3, 1998

(65) Prior Publication Data

US 2001/0031464 A1 Oct. 18, 2001

(51) Int. Cl.[7] .................. G01N 33/543; C12Q 1/68; A61K 38/00; C07H 21/04
(52) U.S. Cl. ................. 436/518; 435/6; 435/DIG. 34; 435/DIG. 40; 435/DIG. 41; 536/23.1; 530/333
(58) Field of Search .................... 435/6, 7.1, DIG. 40, 435/DIG. 41, DIG. 34; 436/501, 518, 531, 528, 529, 534; 530/333, 334; 514/2, 44; 536/23.1

(56) References Cited

U.S. PATENT DOCUMENTS

| 5,565,324 | A | * | 10/1996 | Still et al. ............... 436/518 |
| 5,573,909 | A | * | 11/1996 | Singer et al. ............... 435/6 |
| 5,716,855 | A | | 2/1998 | Lerner et al. ............ 436/533 |
| 5,721,099 | A | * | 2/1998 | Still et al. ............... 435/6 |
| 5,723,218 | A | | 3/1998 | Haugland et al. ......... 428/402 |
| 5,981,180 | A | | 11/1999 | Chandler et al. ............ 435/6 |
| 6,023,540 | A | | 2/2000 | Walt et al. .............. 385/12 |
| 6,210,900 | B1 | * | 4/2001 | Yamashita et al. ......... 435/7.1 |

FOREIGN PATENT DOCUMENTS

| EP | 0 577 092 | | 1/1994 | |
| EP | WO 99 19515 | | 4/1999 | |
| WO | 95/28640 | * | 10/1995 | ......... G01N/33/53 |
| WO | WO 97 14028 | | 4/1997 | |

OTHER PUBLICATIONS

Waggoner, A., "Multiparameter Fluorescence Imaging Microscopy: Reagents and Instruments", *Human Pathology* (1996) 27:494–502.
Speel, E.J., "Sensitive Multicolor Fluorescence In Situ Hybridization Using Catalyzed Reporter Deposition (CARD) Amplification", *J Histochem Cytochem* (1997) 45:1439–1446.
Morrison, L.E., "Two–Color Ratio–Coding of Chromosome Targets in Fluorescence in Situ Hybridization: Quantitative Analysis and Reproducibility", *Cytometry* (1997) 27:314–326.

Urata, Y., "A Three–Dimensional Structure Dissection of Drosophila Polytene Chromosomes", *J Cell Miol* (1995) 131:279–295.
Paddy, M.R., "Time–resolved, in vivo studies of mitiotic spindle formation and nuclear lamina breakdown in Drosophila early embryos", *J Cell Sci* (1996) 109:591–607.
Chen, H., "IVE (Image Visualization Environment): A Software Platform for All Three–Dimensional Microscopy Applications" *J Structural Biol* (1996) 116:56–6–0.
Kam, Z., "Three–dimensional microscopy in thick biological samples: a fresh approach for adjusting focus and correcting spherical aberration", *BioImaging* (1997) 5:40–49.
Swedlow, J.R., "Deconvolution in Optical Microscopy", *Deconvolution of Images in Spectra*, Second Edition, (1997), Academic Press pp. 286–307.
Kirk, G., "Quantitative X–ray imaging of labelled molecules in tissues and cells", *J. Microscopy* (1996) 183:181–186.
Borchardt, A., "Small molecule–dependent genetic selection in stochastic nanodroplets as a means of detecting protein–ligand interactions on a large scale", *Chem and Biol* (1997) 4:961–968.
You, A.J., et al., "A miniaturized arrayed assay format for detecting small molecule–protein interactions in cells", *Chem and Biol* (1997) 969–975.
Vorgt, R.F., "Model System Evaluating Fluorescein–Labeled Microbeads as Internal Standards to Calibrate Fluorescence Intensity on Flow Cytometers", *Cytometry* (1989) 10:294–302.
Beverloo, H.B., et al., "Preparation and Microscopic Visualization of Multicolor Luminescent Immunophosphors", *Cytometry* (1992) 13:561–570.
Napolitano, E.W., et al., "Glubodies: randomized libraries of gultathione transferase enzymes", *Chem & Biol* (1996) 3:359–367.
Keij et al., "Flow Cytometric Characterization and Classification of Multiple Dual–Color Fluorescent Microspheres Using Fluorescence Lifetime," *Cytometry* (1998) 33(3):318–323.

* cited by examiner

Primary Examiner—Padmashri Ponnaluri
(74) Attorney, Agent, or Firm—Morrison & Foerster LLP

(57) ABSTRACT

Particulate labels that can be individually identified comprise particulate supports to which are bound at least two distinguishable signal generating moieties, such as fluorophores emitting at different wavelengths, which signals are detectable and measurable in situ. By varying the ratio and/or amounts of the signal generating moieties, a multiplicity of different and distinguishable labels is obtained. Each different label can then be coupled to a different reagent and the individual interactions of each reagent with a target observed in parallel.

19 Claims, 4 Drawing Sheets

MULTIHUED LABELS

TECHNICAL FIELD

The invention relates to assay methods which utilize unique labeling particles containing signal generating moieties whose ratio can be adjusted. More specifically, the invention concerns particulate labels wherein the hue of the label can be adjusted incrementally.

BACKGROUND ART

It is often desirable to test a sample for reactivity against a multiplicity of reagents. For example, in tissue typing, the ability of cells in a particular tissue to immunoreact with a panel of antibodies raised with respect to marker antigens is required. Genetic testing often involves detecting the polymorphic form of a particular gene by assessing its hybridization to only one of many allelic possibilities. There are also techniques for sequencing by DNA hybridization performed by probing immobilized reference spots of simple sequence DNA with the fragment to be sequenced. In this technique, the ratios of binding of the fragment to be sequenced to each of the simple sequences is unique for each possible sequence in the target fragment. Proteins generated from cDNA libraries representing characteristic expression products of particular cells can be screened for reactivity with various targets. The targets may include antibodies, for example, or small molecule drug candidates.

In all of these cases, either repetitious multiple testing with a variety of reagents is necessary, or the reagents are displayed in an orderly array, such as on a microtiter plate or on a "chip" to assess the reactivity of a sample. In all of these procedures, the association of a particular label with formation of a complex by binding to a component of the sample requires identification of the label by its position in time (for sequential testing) or space (for testing against a panel) or by further measurements on the label, that require its release from the solid particles, e.g., by mass spectroscopy. For example, U.S. Pat. No. 5,721,099 describes solid supports used in multistage synthesis of combinatorial libraries. Labels attached to the solid support identify the structure of the member of the library attached. The reaction history of each particle can be determined by the release of the label and analysis to determine the nature and amount of the tag.

It would be advantageous if a sample could be simply assessed for its reactivity with a multiplicity of reagents without the necessity for physical or temporal separation. The present invention achieves this result by employing labels whose identity can be assessed in situ by their degree of "gray," i.e., a property that can vary by small gradations between extremes over a wide range such as "white" to "black." While visible light is used as an illustration and as a means for explanation for simplicity herein, the invention includes embodiments of "color" which comprise other spectral properties such as radio frequency associated vibrational relaxation times in response to a magnetic field. Any property that can be varied over a wide range, as described above, can be employed. Thus, the nature of the label that is bound to a component of the sample is determinable by direct observation, enabling multiple parallel assays.

Attempts at multicolor labeling in a single sample have been made, most notably in "painting" chromosomes with labels of different color, a technique known as fluorescent in situ hybridization (FISH) with different colored labels for each chromosome. This technique has also been used to paint cells with different surface receptors by using binding ligands bearing different fluorophores. A summary of such approaches is set forth in Waggoner, A. et al., *Human Pathology* (1996) 27:494–502. The ability of the human eye to distinguish hues created by mixtures of different color components (although not with varied ratios of the same mixture of components) was demonstrated by Speel, E. J., et al., *J Histochem Cytochem* (1997) 45:1439–1446. Adaptation of this approach to oligonucleotide labels wherein dyes were applied at varying ratios to generate a number of different hues for the purpose of painting chromosomes was described by Morrison, L. E., et al., *Cytometry* (1997) 27:314–326. Although the labels are not particulate, and thus do not permit maximum signal intensity or the distinctive shape signal of uniform beads, this work does demonstrate that microscopic techniques can effectively detect and sort the hues generated when varying ratios of fluorophores are applied to a single label. As described in the catalog from Molecular Probes (Seattle), a microsphere of 100 nm diameter can be loaded with fluorescein to give an intensity equivalent to 7400 free fluorescein molecules with loading controllable to an accuracy better than plus or minus 5 percent.

The present invention offers the versatility of reagents and intensity of signal available through multihued beads wherein the particulate supports bearing signal generating moieties are provided specific differentiable signals by virtue of these varying ratios.

DISCLOSURE OF THE INVENTION

Labels that can be identified by direct observation of their hue represent a great convenience in assays where multiple reactivities must be observed. The labels of the invention are particulate materials which contain at least two different signal generating moieties—for example, each providing light of a particular wavelength range either by reflectance or fluorescence. Thus, in one embodiment, an individual particle will contain moieties that emit or reflect light of different colors. By adjusting the relative amounts of the different moieties attached to the particle, the perceived "hue" of the label will be different and it can be distinguished from other labels containing these moieties in different ratios. Effective use of these labels requires separate means for detection for each of the moieties coupled to the particle. Preferably, the particles contain at least three moieties which generate different wavelengths with a corresponding number of detection means.

Thus, in one aspect, the invention is directed to a label which comprises a particulate support to which is bound at least two signal generating moieties, which moieties generate signals that can be distinguished in situ, such as light of different wavelengths. These labels are distinguishable by any instrumentation which contains separate means for detection for each of the at least two in situ signals generated. In general, separate detectors may be employed; however, a single detector may be employed using appropriate filters or other means, such as a prism or grating, to permit a single detector to perceive separately multiple signals, such as different wavelength ranges.

In another aspect, the invention is directed to a collection of labels of the type described above wherein the ratio of the moieties differs from label to label in the collection. Typically, this collection of labels provides identifiable members that number at least twenty, preferably one hundred, more preferably five hundred, and still more preferably at least one thousand. Thus, if the reliability of detection of each color is plus or minus 10 percent, 10 gray labels exist for each signal and therefore 100 hues can be distinguished when two signal generating moieties are included in each label. For use in analyzing a sample, each label will further be coupled to a different reagent.

In still another aspect, the invention is directed to a system for assessing the reactivity of a sample with a multiplicity of reagents coupled to labels, which system comprises the collection of labels bound to reagents described above along with separate detectors or their equivalents for the signals generated by each different moiety that is present on the particulates in the collection of labels.

In still another aspect, the invention is directed to methods of assessing the reactivity of components in a sample using the assay system described above.

MODES OF CARRYING OUT THE INVENTION

In a preferred embodiment, the labels of the present invention take advantage of the availability of detectors which can sense the intensity of light of particular wavelengths or wavelength ranges. Typical devices of this type are currently commercially available as charge coupled device (CCDs) equipped with standard color filters as used in camcorders for home videos. Higher sensitivity and reliability scientific grade CCD devices and filters are also available. A single CCD can be thus designed to detect only a narrow wavelength band of light, so that detectors can be obtained for, for example, red, green or blue light only. The CCD detectors are currently employed in wide field fluorescence microscopy, a technique which provides high resolution in three dimensions as well as time resolution. High precision instruments of this type are commercially available from Applied Precision (Seattle, Wash.) and are described in a series of papers authored by a group headed by John W. Sedat. These publications include Urata, Y., et al., *J Cell Miol* (1995) 131:279–295; Paddy, M. R., et al., *J Cell Sci* (1996) 109:591–607; Chen, H., et al., *J Structural Biol* (1996) 116:56–60; Kam, Z., et al., *BioImaging* (1997) 5:40–49. A summary of these techniques is provided in a chapter by Swedlow, J. R., et al., in "Deconvolution of Images in Spectra", Second Edition, (1997) *Academic Press*, pages 286–307.

This instrumentation provides fluorescence excitation and capacity for detection of three separate wavelengths of light. In current applications, these instruments can be and are used to detect the reaction of components in a sample with three different reactants each coupled to a latex bead having a color corresponding to one of the CCD detectors. Such beads are available commercially in several different colors of fluorophores with high uniformity in size and fluorophore doping levels from Flow Cytometry Standards Corp. (Puerto Rico); Molecular Probes (Seattle, Wash.); Polysciences (Warrington, Pa.); and from the Los Alamos LS-5 Cytometry Group, among others.

Figure 1:
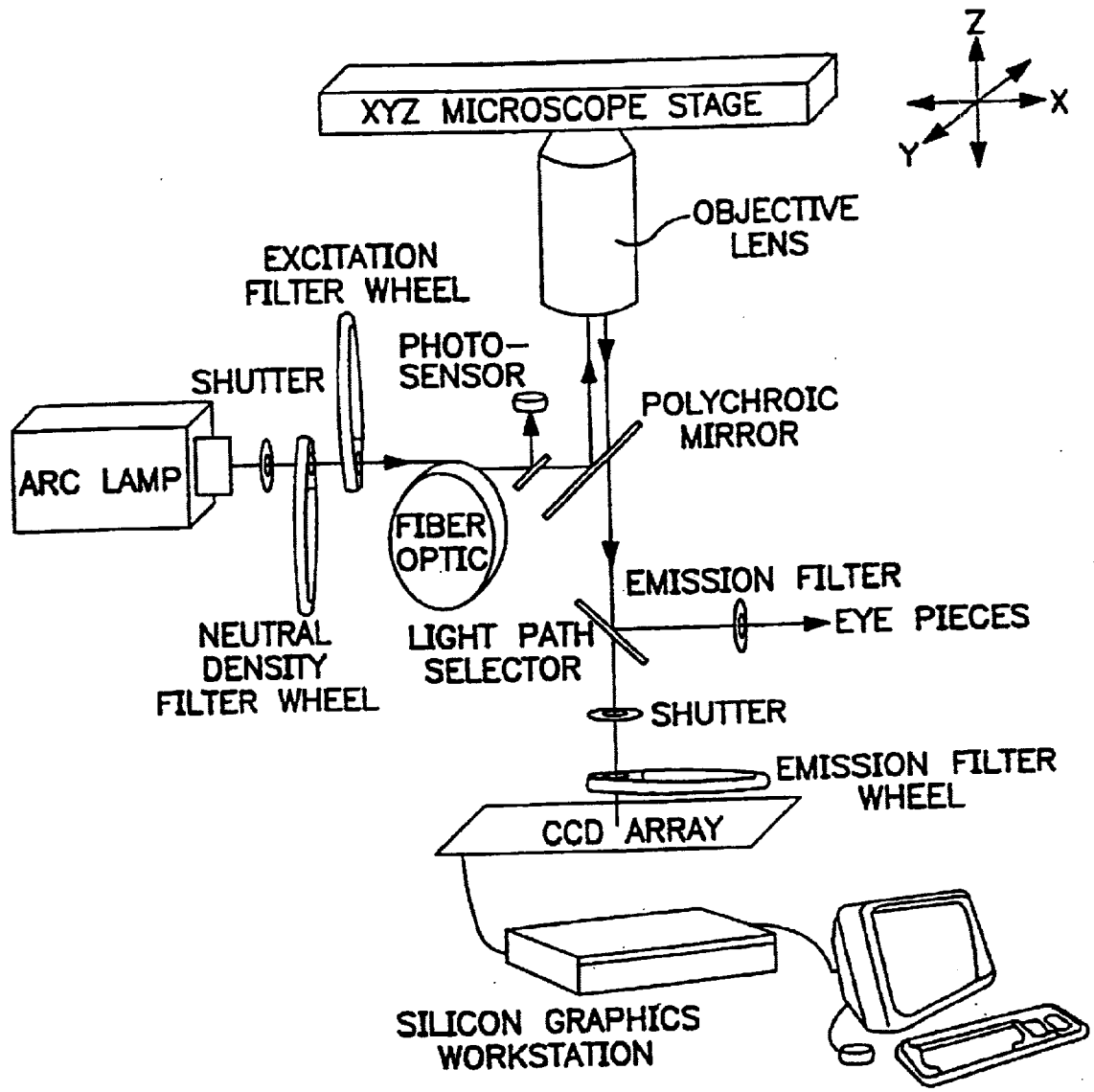
FIG. 1 is a diagrammatic representation of a system for detecting the label reactivity with a sample.

A schematic of a typical wide field fluorescence microscope with a single CCD detector and filter wheels is shown in FIG. 1. The multihued labels of the invention are conveniently read in this system. Fixed filters and separate CCD detectors, as diagramed in FIG. 3, simplify image registration and speed of data collection.

The Multihued Labels

The present invention multiplies the number of reagents that can be separately detected under these conditions by systematic and precise doping of particulate supports with signal generating moieties, typically fluorophores, of different colors corresponding to the CCD detectors employed, at specified ratios. Particles with different ratios of the fluorophores generate different detection signals in this system. Because the ratios of the fluorophores can be varied at will, up to a point where a forced proximity of the dyes leads to quenching, many different "hues" can be generated in a collection of labeled particles, each particle type having a unique ratio and/or amount of color generating moieties. If each different label is coupled to a different reagent, the collection can be used to run multiple assays at once as each particle can be identified by the hue of the light it generates.

As used herein, the term "label" is generally used to describe a particulate support to which has been bound an appropriate array of signal generating moieties. The signal-generating moieties must be such that the signals are detected in situ on the particulate support. Thus, it is unnecessary to detach the signal-generating moieties from the support in order to ascertain their ratio. Their ratio is read directly by means of the "hue" of the label. Color is a preferred signal. The labels of the invention contain at least two, and preferably at least three, distinguishable signal generating moieties. The ratios and amounts of the signal generating moieties provide each label with a particular "hue"—i.e., a particular combination (ratio and absolute intensity) of the at least two and preferably at least three signal generating moieties. When used, the label will be coupled to a "reagent"—i.e., a substance associated with the label to detect a complementary analyte. For use in the convenient assays of the invention, a collection of labeled reagents will be required—i.e., a "multi-hue array"—a set of labeled reagents for which the hue corresponding to each reagent is well defined.

As visible light is a particularly convenient way to generate a particular "hue," this embodiment of the invention is exemplified herein. However, other signal generating moieties can be employed or an indirect method to generate visible light may be used. For example, particles may be provided with radioisotopes having different energies along with insoluble scintillants. $^3$H and $^{35}$S contained in a single particle with insoluble scintillants give distinguishable photon bursts, as is the basis for pulse height analyzers used in standard scintillation counters. Alkaline phosphatase and horseradish peroxidase contained at specific ratios with appropriate substrates provide different signals, including those generated by chromophores or, more directly, different electrochemical reducing powers. In addition, heavy atom clusters of different materials, for example colloidal gold dots versus ferrite rods offer different scattering characteristics with respect to electron microscope beams. Kirk, G., et al., *J. Microscopy* (1996) 183:181–186. The preferred "color generating" moieties are typically fluorophores, but they can also generate a characteristic wavelength either by reflectance (simple dyes) or by emission (fluorophores or de novo light-generating compounds such as a luciferase or other chemiluminescent system). A number of chemiluminescent systems are known in the art such as horseradish peroxidase-based generation of chemiluminescent products. Suitable absorbing dyes include alizarin red, thiazole yellow, naphthyl green Y, indophenol blue, Gentian violet. Suitable fluorophores include dansyl, green fluorescent protein, fluorescein, Hoechst, Texas Red, merocyanines, and the like. A number of dyes covering a wide range of wavelength emissions have been developed as described in Waggoner, A. et al., *Human Pathology* (1996) 27:494–502, incorporated herein by reference. In addition to fluorescent dyes, phosphorescent materials may also be employed which adds the advantage that time resolved fluorescence distinguishes signals that would be equivalent averaged over a longer detection period. Light emitting systems which do not require excitation by external radiation include the combination of radioisotope and scintillant embodiment set forth above as well as the enzyme systems that generate distinguishable chromophores or act on spontaneously chemiluminescent substrates.

Conceptually, simply varying the ratio of fluorophores is the most straightforward way to alter hue. However, more sophisticated approaches include selecting the dyes so that they interact in predetermined ways, for example by energy transfer wherein excitation at the excitation maximum for a first dye results in a non-radiative transfer to a second dye which then emits. Different input ratios with respect to the excitation peaks of the two dyes result in different outputs under the appropriate conditions. Further, if one dye is placed on the interior of the particle and the other on the exterior, a hue will be created that is distinct from that obtained when the two dyes are mixed uniformly throughout the particle, or when the positions of the dyes are reversed.

The supporting particles are typically 0.1–1 μm in diameter and are preferably latex. However, smaller particles may also be used. Generally, 50 nm (0.05 μm) is considered an approximate minimum; it has been possible in some contexts to use particles as large as 5 μm, although this is not preferred. The use of larger particles results in lower diffusion rates and thus, effectively, less efficient and less vivid labeling. A preferred range is 100–500, preferably 100–300, and more preferably 100–200 nm diameter particles. The particulate supports are generally spherical, and the microscopic techniques employed can distinguish spherical shapes from other general outlines. However, other particulates may also be used, such as polyvinyl, polysaccharides such as dextran and sepharose, polymers such as cross-linked polyacrylamide and polyethylene glycol and the like. Silica gel particles may also be used. Any particulate that has suitable physical properties (does not spontaneously aggregate, adhere, or otherwise fail to behave as an independent particle) and which can be suitably derivatized with the color generating moieties and with the test reagent may be used.

The construction of the particle itself affects the hue detected. In addition to differences attributed to the size of the particle, as indicated above, the shape will determine the nature of the signal. Shapes can vary along the continuum of sphere to oval to rod to string, for example. Star shapes or other arbitrarily shaped particles can be created by x-ray lithography so as to have a distinctive point spread function. Thus, any aspect of the labeled particle that provides a distinctive signature can be used. As an example, a refractive index is affected by the density and composition of the particle itself. In short, two particles with the same ratio and absolute intensity of fluorophores but distinguishable shapes have distinctive hues as defined herein.

Finally, notwithstanding the desirable characteristic listed above that the particles useful in the invention do not aggregate, controlled aggregation may be employed in appropriate instances to obtain size variance based on the proportions of the constituent particles. For example, if the particles are derivatized with bifunctional or monofunctional cross linkers, different ratios of bi and mono linkers in mixtures of particles will lead to aggregates of different sizes. This approach may be particularly attractive in in vivo applications wherein small particles, even individual dye molecules, are more readily transported into cells. These can then be designed to self assemble into particulates by virtue of enzymatic activity or by photolysis.

The nature of the coupling techniques for both the color generating moieties and the reagent will depend on the nature of the supporting particle, the nature of the color generating moiety, and the nature of the reagent. Suitable linking techniques are well known in the art. By way of example only, if the reagents are proteins, they may be recombinantly produced with a hexahistidine sequence or with an epitope, such as a FLAG epitope which can then be bound to particles which are manufactured to incorporate a nickel chelator or an antibody to the epitope. Standard linking techniques applicable to a multiplicity of substances and to the functional groups available on particulate supports include disulfide linkages generated from sulfhydryl moieties on each component and amide linkages generated from carboxyl and amino functional groups. Other examples include homobifunctional and heterobifunctional linkers as set forth in the catalog for Pierce Chemical Company, Rockford, Ill.

Rather than a covalent attachment of the reagent to label, the reagent may simply be physically associated with it, for example by being trapped in a thin layer of agar coating the particulate label. The reagent is released when the sample to be analyzed is contacted with a collection of labels by melting the agar. The physical proximity of the label then serves to identify the reagent that reacts successfully with a component of the sample. Such an approach exploiting physical proximity was described by Borchardt, A., et al., *Chem and Biol* (1997) 4:961–968; You, A. J., et al., ibid. 969–975. These documents also describe photolabile linkers and use of an aerosol generator to create droplets comprising coated beads.

As stated above, the manner of construction of the labels depends on the nature of the signal-generating moiety and the chemical composition of the solid support. One exemplary procedure is set forth in Vogt, R. F., et al., *Cytometry* (1989) 10:294–302 which describes a linear relationship between moles of FITC added to latex beads and integrated intensity of fluorescence observed in a cell sorter. Using the techniques there described, a wide multiplicity of hues can be obtained by varying the amounts of each signal-generating moiety.

In contrast to the present invention, the description of preparing colloidal particles each carrying a single inorganic phosphor, as set forth in Beverloo, H. B., et al., *Cytometry* (1992) 13:561–570, emphasizes that the particles labeled with individual reagents should be supplied sequentially to the sample rather than as a mixture. Sequential supply is needed in order to provide an unambiguous picture since the ratio of antigens determines the ratio of captured antibody. On the other hand, the labeled reagents of the present invention may readily be supplied to the sample as a mixture as they are readily distinguished by the different hues of their labels examined individually.

Figure 2:
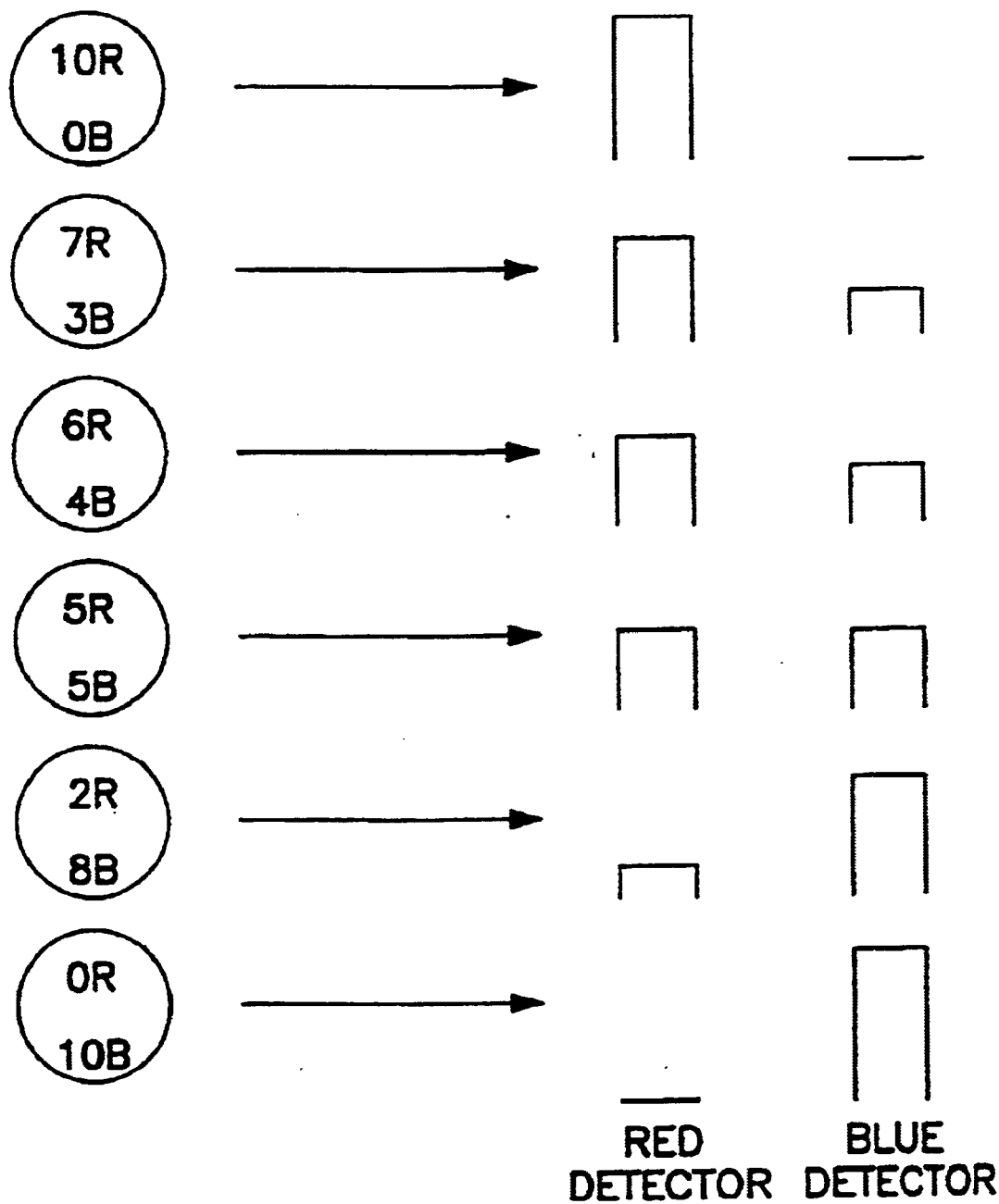
FIG. 2 diagrams the composition of a representative sample of labels of varying colors.

Each label, then, will contain at least two different signal generating moieties, typically fluorophores, and for use in assays will be coupled to the relevant reagent. Each different reagent will be coupled to a different label. The invention method for generating a multiplicity of different labels is illustrated in FIG. 2 for beads with only two fluorophores. In this illustration, the ratio of the red light generating moiety to blue light generating moiety is varied over a series of ten levels for each color. This results in a hundred different "hues"—i.e., ratios and intensities. As shown in FIG. 2, different signals will be obtained depending on the ratio and/or amount of red and blue color generating moieties. The ratios and intensities of the responses in the red and blue detectors is indicative of the label being measured. Since the detectors can measure intensity as well as color per se, labels which contain a ratio of 10 red to 2 blue can be distinguished from labels that contain 5 red to 1 blue. An additional multiplier of the number of different possible labels can be added by varying the size of the particulate support which can be independently measured in the microscope system described above.

Similar extensions can be made with additional colors of fluorophore in multiple dimensions. The multiplicity of colors available is limited only by the availability of suitable discrimination capabilities with respect to light generation and detection. Thus, if three color generating moieties are included, each of which can be reliably classified into ten shades of gray, labels with 1,000 different hues can be generated. If each color generating moiety can be reliably classified into 100 levels of gray, 1 million different hues are enabled for a collection of these labels.

Uses of the Multihued Labels

For use, generally, the labels are attached to reagents so that each individually hued label is coupled to a different known reagent. The nature of the reagent can then be ascertained from the hue of the label to which it is attached. The reagent will be any substance or compound that is reactive with a potential target or analyte. Suitable reagents, then, include proteins, carbohydrates, nucleic acids, including oligonucleotides, and the like, depending on the nature of the assay that is to be run.

One particularly useful set of reagents comprises a class of proteins typically known as "antibodies." This class offers the generation of a large variety of binding regions of varying specificities. The classical "antibody" specific for a particular antigen is obtained through immunization of a suitable vertebrate and recovery of polyclonal antibodies from the plasma or serum or recovery of monoclonal antibodies through hybridoma technology. It is well known that antibodies as obtained in this way are not required in their entirety for binding specificity; only the variable regions need be present. Thus, included within the term "antibodies" as used herein, are fragments of the antibodies such as $F_{ab}$, $F_{ab'}$, and $F_{(ab')_2}$ fragments. In addition, the availability of recombinant techniques makes possible altered and species-adapted forms of specifically binding regions, such as single-chain $F_v$ "antibodies." More generally, "antibodies" is used herein to refer to any group of proteinaceous compounds which can contain a variable binding region. Thus, the solvent-exposed loop present in many proteins can be altered in structure using mutagenic techniques to afford a wide variety of binding specificities. Napolitano, E. W., et al., *Chem & Biol* (1996) 3:359–367. In addition, peptides and other oligomers with a wide variety of specificities can be constructed using combinatorial techniques to obtain panels of paralogs with widely differing binding specificities. Kauvar, L. M., U.S. Pat. No. 5,340,474 (1994), As used herein, "antibodies" includes all such variably binding proteins.

In addition to proteins, nucleic acids, in particular oligomers, can be widely varied in binding specificity. A number of techniques are available for generating oligomers of differing binding specificities; e.g., the Selex technique.

Of course, the nature of the reagent depends on the nature of the application. Antibodies are useful in tissue-typing and other diagnostic assays, peptides generated from cDNA libraries are useful in assessing receptor binding, for example. Reagents which are oligonucleotides are useful in assays based on complementary chain hybridization. Reagents that are combinatorial chemistry library members are useful in screening for medicaments. The choice of reagent depending on the purpose and type of assay is well within ordinary skill in the art.

Thus, the multihued labels of the invention are useful in a variety of assays, especially those where multiple reactivities must be assessed. One example, as noted above, is tissue typing where standard serology defines major types and subtypes. The labels coupled to diagnostic antibodies may be designed for example so that larger beads, each having three fluorophores at different ratios are coupled to different antibodies representing major classes, thus permitting the identification of up to one thousand major classes. Similarly, small beads each having three fluorophores can distinguish among one thousand subtypes. Thus, in theory, a single tissue specimen could be classified with regard to a million sera. As a practical matter, however, only about one thousand separate antibodies would be needed to do an adequate classification.

In this, and in other applications, it will be necessary to fix tissue to be tested. Standard fixation conditions which include, for example, glutaraldehyde are less favored since it is desirable to provide permeable surfaces for the labels of the invention. Variation of the fixation conditions, further, may result in discrimination among labels of different types, which adds another dimension of distinguishability. Polymers particularly useful for fixing tissue samples under these circumstances are typified by those manufactured by Landec (Palo Alto, Calif.) which exhibit sharp transitions between gel and sol states over a given temperature range. The differences in transition temperatures between these polymers are achieved by varying derivatization, such as hydroxylation. Fixing the sample is achieved by infiltrating the tissue with a polymer at above its transition temperature—i.e., in the sol state, and then fixing for sectioning by cooling. By varying the proportions of the polymers with different transition temperatures, the degree of permeability can be regulated in the resulting sample, generally by rewarming after sectioning. Further temperature manipulations can vary the permeability as desired.

In another application, a cDNA library is tested for proteins that interact with a target by producing a multiplicity of beads each with a different "hue" i.e., ratio of color generating moieties and/or different intensity of color generation and each with a different protein from the library. This set of multihued beads can then be tested all at once for binding to a particular target, and the successful interaction identified by the signal generated of the bead to which it is attached. The target may be an immobilized natural product or receptor; alternatively, this system may be adapted to detect interaction between two libraries of proteins or two collections of substances generally, in an analogy to the yeast two hybrid assay.

The assay system characterized by the labels of the invention can also be adapted for use in nucleotide sequencing by DNA hybridization, as described in U.S. Pat. Nos. 5,202,231 and 5,525,464. In this adaptation, each reference simple DNA sequence is attached to a different label. The collection of labeled sequences is then applied to multiple copies of the fragment to be sequenced. Typically, the fragment is immobilized and probed with the collection of labels.

Figure 3:
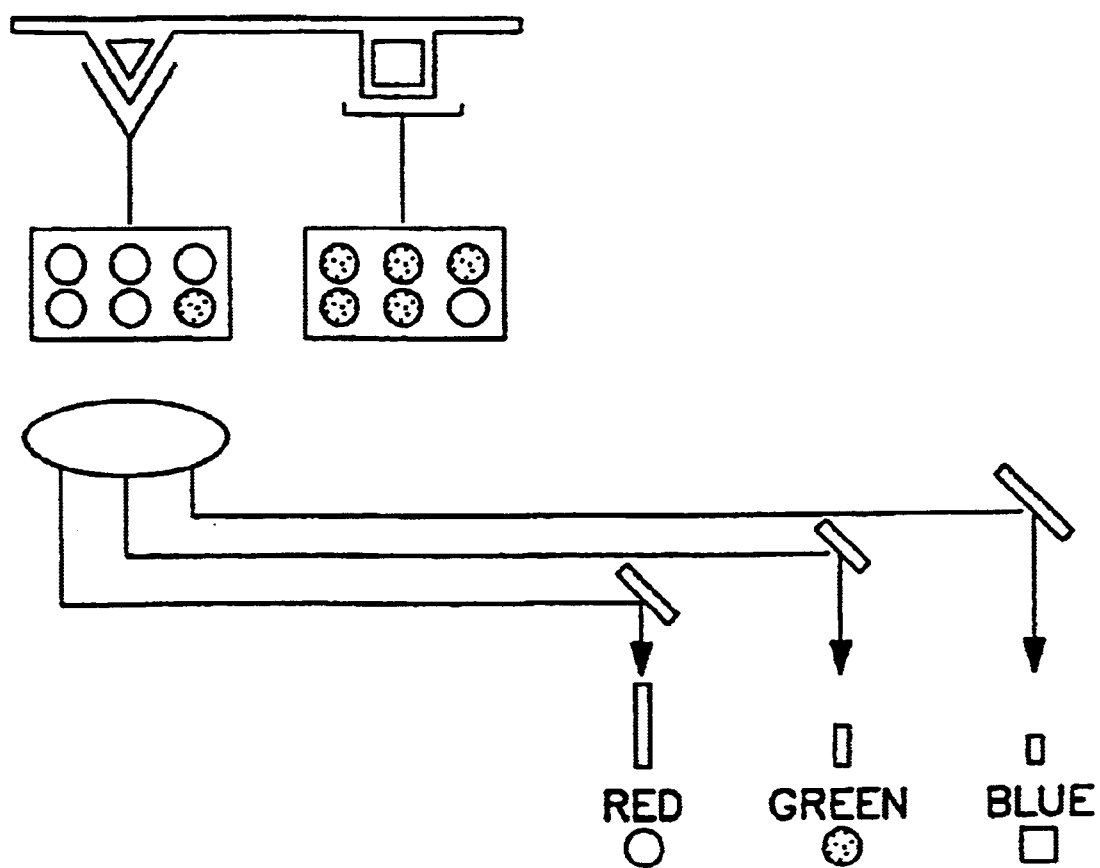
FIG. 3 diagrams an assay system for analyzing a solution for a multiplicity of analytes in which each reagent with its corresponding label is imaged independently.

The collection of labels, each coupled to a different nucleotide sequence, can also be used in genetic testing. In one design, larger particulates, for example, contain long nucleotide sequences complementary to conserved regions of the gene and are used to define whole genes under stringent hybridization conditions whereas another set of smaller particulate based labels containing shorter nucleotide sequences may be used to detect mutations in regions of polymorphism under hybridization conditions where even a single mismatch leads to reduction in signal. The labels may be read in a high precision wide field microscope with CCD detectors appropriate to the color generating moieties which comprise the label without the need of a washing step because the sharp focal plane of such instrumentation permits distinction between labeled sequences which are hybridized to surface-immobilized target and those which are not. Thus, samples from a series of time points, for example, can be concurrently assayed for expression of many genes. Similarly, examination of gene expression in embryonic development, arrested at defined time points is possible, allowing spatial and temporal patterns of expression to be simply determined. FIG. 3 diagrams this approach schematically. The solid triangle and solid rectangle represent two analytes immobilized in the focal plane, for example, in a tissue slice. The presence of each analyte in the tissue slice is detected via the labels bearing reagents for each of these analytes.

Still another instance where analysis with respect to multiple reagents is desired is in the screening of combinatorial libraries. Each member of the combinatorial library is attached to a label with a different ratio and/or quantity of color generating moieties. Thus, the identity of the compound in the library which is capable of binding to target can be ascertained by the intensity and color generated by its label. The addition of the color generating moieties to the particulate label can be carried out in conjunction with the synthesis of the library members so that the amount or ratios of the color generating moieties are coordinated with the structural features of the library members. Alternatively, the color-generating moieties may be attached via labile linkers and different amounts of label removed by controlled degrees of photolysis or chemical cleavage.

One application of a combinatorial library is a library of recombinant antibodies having randomized binding sites. This library, with members coupled to labels of different ratios of color generating moieties and/or light intensities may be used to probe protein libraries, for example those obtained by expression of cDNAs which have been transferred to nitrocellulose.

To prepare such a library of labeled antibodies, a convenient approach is as follows:

The particulate supports, initially uniformly labeled with color generating moieties that are coupled to the particulates through linkages that are lysed by specific wavelength activation are spread over a surface. Filters can then be employed in a specific pattern over the surface so as to generate a multiplicity of ratios of the color generating moieties and of total amounts thereof. The result is a two-dimensional surface where the labels are varied in a systematic way. The surface is then overlain with individual colonies each producing a different recombinant antibody. Preferably, the antibodies are modified by hexahistidine or the FLAG epitope to make their linkage to the corresponding label more facile. The collection of antibodies labeled with the multihued array then can be pooled and used to screen a sample for antigens having reactivity with the these antibodies. Recovery of the cells producing the successful antibodies is accomplished by reading the hue of the label and referencing each to the two-dimensional surface pattern where that hue was created, and onto which the clones were deposited. In this way, antibodies specifically reactive with antigens expressed in situ can be identified for subsequent diagnostic uses.

Similar protocols may be used to determine specific interactions of proteins or peptide members of two different libraries containing nucleotide sequences in a manner analogous to the yeast-to-hybrid assay. The interaction of the two proteins can be modified by intermediate linkers so that the interaction of proteins in one library with small molecules, for example, in another, may also be assessed. Interaction between nucleotide sequences and proteins, such as enhancers and transcription factors, can also be elucidated in this way.

The protein members of the combinatorial library need not, of course, be antibodies but can, instead, be the products of a cDNA library. Thus, the labels and methods of the invention permit screening of cDNA×cDNA libraries, for example to identify specific antibody interacting proteins for nearly all genes identified by the human genome project. Matching DNA promoter sequences with transcription factors are similarly enabled as described above.

More generically, the methods of the invention can be used to assess secreted proteins in general. Cells which secrete these proteins are plated in two-dimensions and covered with a capture layer which includes, for example, DEAE-agarose combined with CM-agarose which together will bind most proteins. Alternatively, the capture layer may include an antibody or other specific binding pair member complementary to the secreted protein. The secreted and captured proteins can be tested against an array of labeled antibodies directed to epitopes on the captured proteins that remain exposed.

Figure 4:
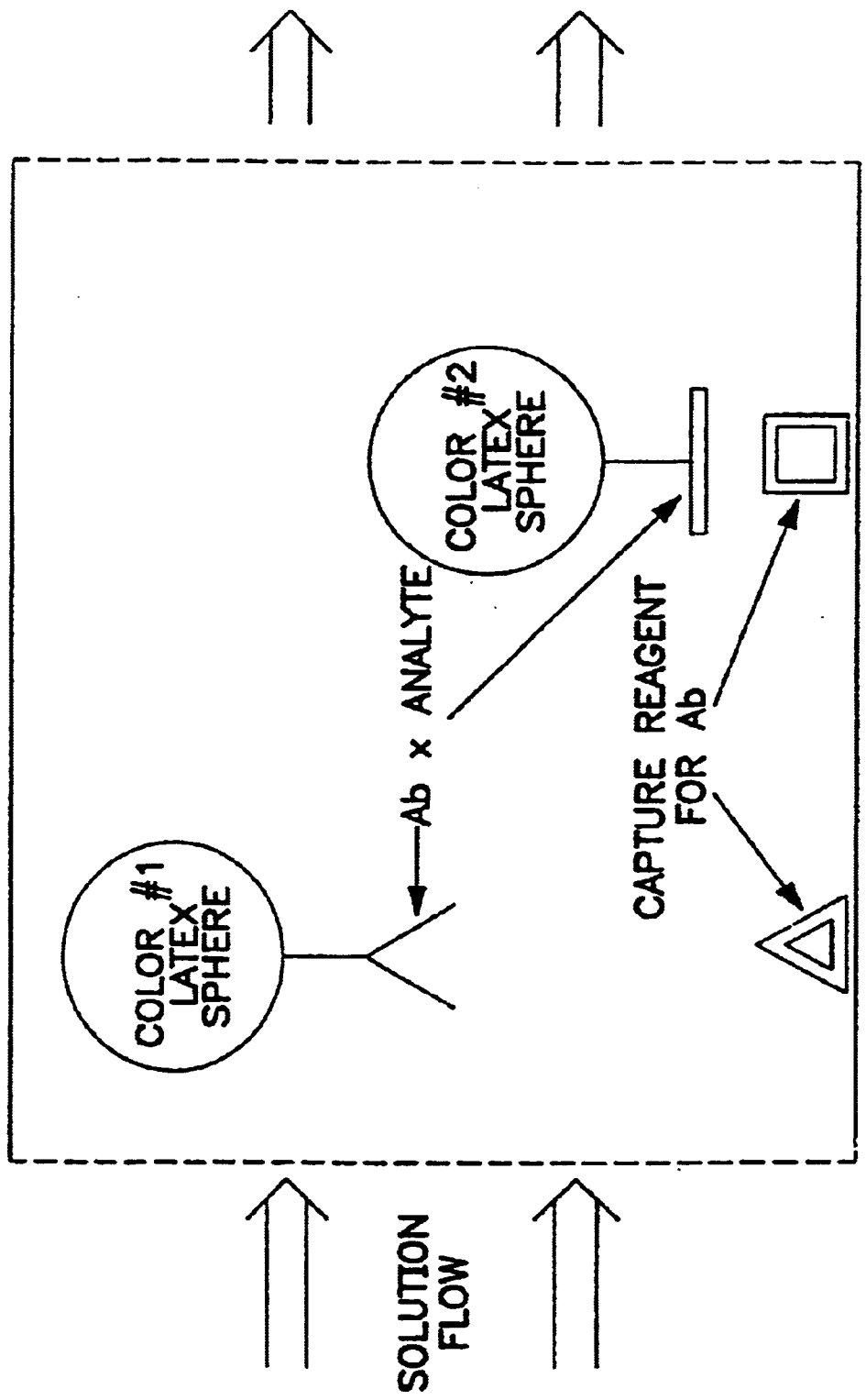
FIG. 4 diagrams a continuous operation biosensor.

Another specific application of the methods and materials of the invention relates to the use of a biosensor which can be designed for continuous analysis of an analyte solution. The analyte solution is passed through a mesh containing a collection of labeled reagents where the size of the mesh pores is too small to permit the labeled reagents to pass; thus, the labeled reagents are trapped within the sensor. The compartment defined by the mesh further contains competing analogs of the analyte contained in the solution in a position where label can be detected—i.e., for example, the focal plane of a microscope. Thus, the label is only perceived if it is captured by the competing analog of the analyte in the appropriate position. As the sample to be analyzed passes through the compartment defined by the mesh, any analyte in the sample competes for label with the analogs constrained to the focal plane, thus releasing label from the location in which it can be detected. A diminution in detectable label thus indicates the presence and amount of analyte in solution. As a collection of multihued labels can be used, a multiplicity of analytes can be assessed simultaneously. This is shown schematically in FIG. 4. Such a system is useful for continuously monitoring the levels of a drug and its metabolites in blood and urine, for example.

What is claimed is:

1. A spatially defined arrangement of particulate different labels wherein each different label comprises a particulate support to which is coupled at least two signal generating fluorophores wherein each of said fluorophoresemits a detectable signal different from that emitted by the other(s) and wherein the magnitude of each of said emitted signals is varied among said different labels whereby each different label is thereby characterized by a different hue, which hue is detected and distinguished from the other hues in the multiplicity of labels whereby each different label is identifiable in situ, and wherein said arrangement of particulate labels is displayed on a surface to permit determination of the spatial position of said labels by means of fluorescence microscopy; and wherein each different label is associated with a different reagent.

2. The arrangement of labels of claim 1, wherein each particulate support is coupled to at least three aid signal generating fluorophores.

3. The arrangement of labels of claim 1, wherein the particulate support is latex bead.

4. The arrangement of labels of claim 1, wherein each reagent is an antibody.

5. The arrangement of labels of claim 1, wherein each reagent is a peptide generated from a cDNA library.

6. The arrangement of labels of claim 1, wherein each reagent is a substance in a combinatorial chemistry library.

7. The arrangement of labels of claim 1, wherein each reagent is an oligonucleotide.

8. The arrangement of labels of claim 1, wherein each reagent is linked to the label by a covalent linkage.

9. The arrangement of labels of claim 8, wherein the covalent linkage is a disulfide or carboxamide linkage.

10. The arrangement of labels of claim 1, wherein each reagent is linked to the label by a noncovalent linkage.

11. The arrangement of labels of claim 10, wherein the noncovalent linkage is an epitope/antibody linkage, or a histidine/chelated-Ni linkage, or comprises an agar layer in which the reagent is trapped.

12. The arrangement of labels of claim 2, wherein each reagent is an antibody.

13. The arrangement of labels of claim 2, wherein each reagent is a peptide generated from a cDNA library.

14. The arrangement of labels of claim 2, wherein each reagent is a substance in a combinatorial chemistry library.

15. The arrangement of labels of claim 2, wherein each reagent is an oligonucleotide.

16. The arrangement of labels of claim 2, wherein each reagent is linked to the label by a covalent linkage.

17. The arrangement of labels of claim 16, wherein the covalent linkage is a disulfide or carboxamide linkage.

18. The arrangement of labels of claim 2, wherein each reagent is linked to the label by a noncovalent linkage.

19. The arrangement of labels of claim 18, wherein the noncovalent linkage is an epitope/antibody linkage, or a histidine chelated-Ni linkage, or comprises an agar layer in which the reagent is trapped.

* * * * *